United States Patent
Giordano et al.

(10) Patent No.: US 6,171,310 B1
(45) Date of Patent: Jan. 9, 2001

(54) DEVICE AND METHOD FOR HANDLING AN IMPLANT COVERING A BONE TUNNEL

(75) Inventors: Nicola Giordano, Villingen-Schwenningen; Karl-Ernst Kienzle, Immendingen; Juergen Eichhorn, Mitterfels/Scheibelsgrub, all of (DE)

(73) Assignee: Aesculap AG & Co. KG, Tuttlingen (DE)

( * ) Notice: Under 35 U.S.C. 154(b), the term of this patent shall be extended for 0 days.

(21) Appl. No.: 09/280,333

(22) Filed: Mar. 29, 1999

(30) Foreign Application Priority Data

Apr. 1, 1998 (DE) .............................................. 198 14 564

(51) Int. Cl.$^7$ ..................................................... A61B 17/56
(52) U.S. Cl. ................................................. 606/60; 606/53
(58) Field of Search ............................... 606/60, 53, 102, 606/103, 104, 72, 86, 88; 600/587; 623/13.13, 13.14

(56) References Cited

U.S. PATENT DOCUMENTS

| | | | |
|---|---|---|---|
| 4,712,542 | * | 12/1987 | Daniel et al. |
| 5,071,420 | * | 12/1991 | Paulos et al. ........................... 606/99 |
| 5,449,361 | * | 9/1995 | Preissman ............................. 606/103 |
| 5,713,897 | * | 2/1998 | Goble et al. ........................... 606/53 |
| 5,797,913 | * | 8/1998 | Dambreville et al. ................. 606/72 |
| 5,944,724 | * | 8/1999 | Lizardi ................................. 606/104 |
| 5,980,473 | * | 11/1999 | Korakianitis et al. ............... 600/587 |
| 6,001,106 | * | 12/1999 | Ryan et al. .......................... 606/102 |

FOREIGN PATENT DOCUMENTS

| | | |
|---|---|---|
| 77 07 950 | 4/1978 | (DE) . |
| 35 05 567 | 6/1986 | (DE) . |
| 0 361 756 | 4/1990 | (EP) . |
| 0 556 571 | 8/1993 | (EP) . |
| WO 94/09708 | 5/1994 | (WO) . |
| WO 98/01091 | 1/1998 | (WO) . |

* cited by examiner

Primary Examiner—Jeffrey A. Smith
(74) Attorney, Agent, or Firm—Barry R. Lipsitz

(57) ABSTRACT

In order to be able to adjust the tension of a ligament replacement implant in a controlled manner, a device is suggested for handling an implant which can be placed against a contact surface of a bone and thereby covers a tunnel in the bone and fixes in position at least one thread extending in the tunnel, this device being characterized by releasable spreading elements on the device, with which the device can be connected to the implant in a locking position of the spreading elements in such a manner that as a result of rotation of the device this implant can be turned in relation to an axis defined by the tunnel and, in addition, be lifted away from the contact surface in the direction of this axis.

26 Claims, 4 Drawing Sheets

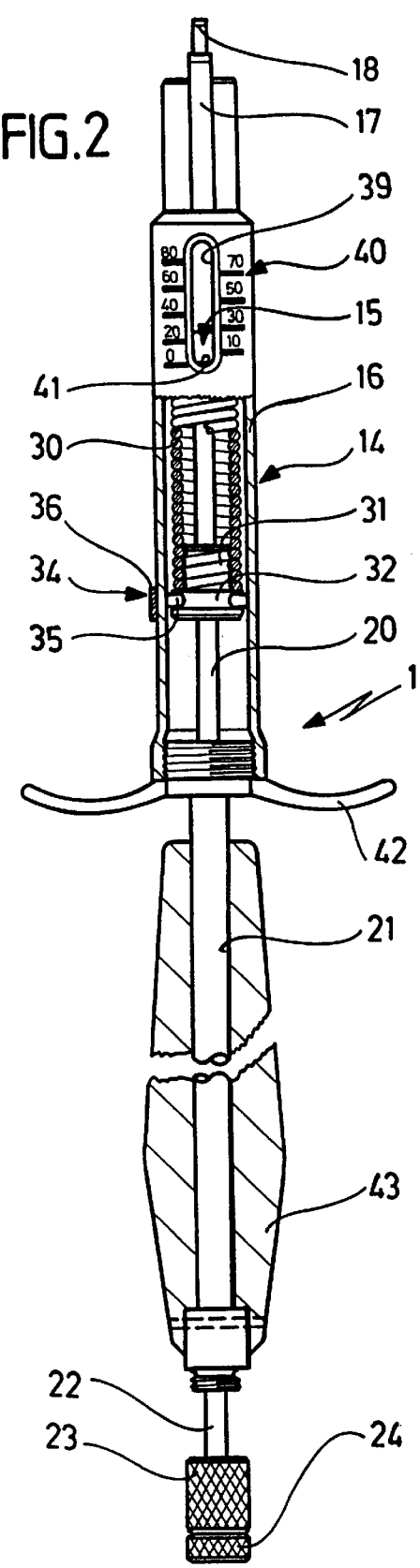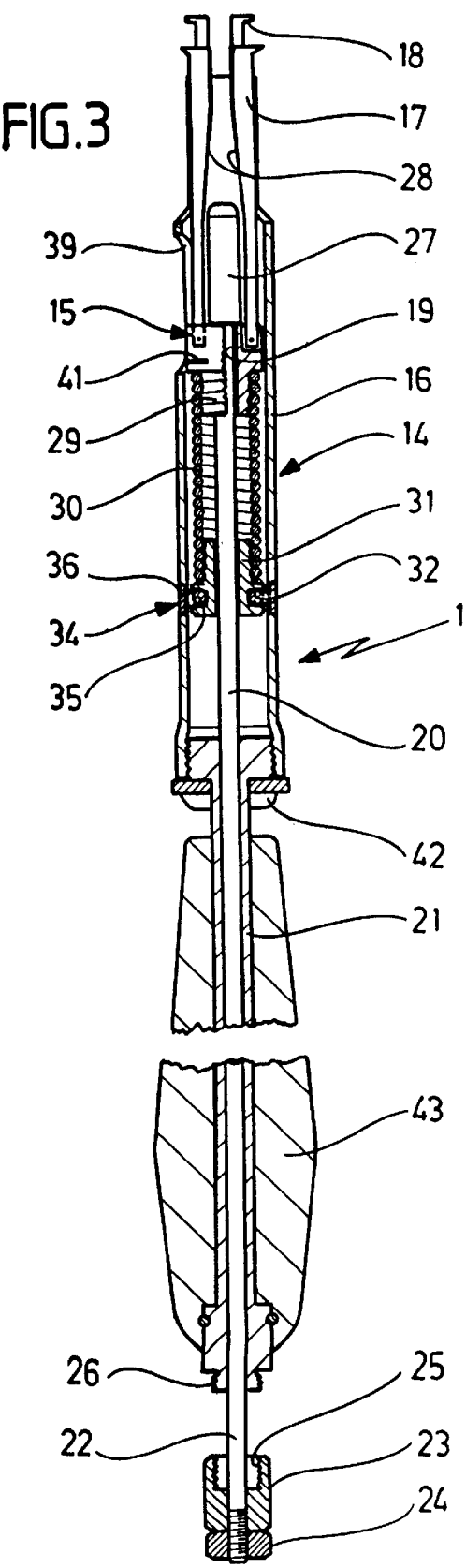

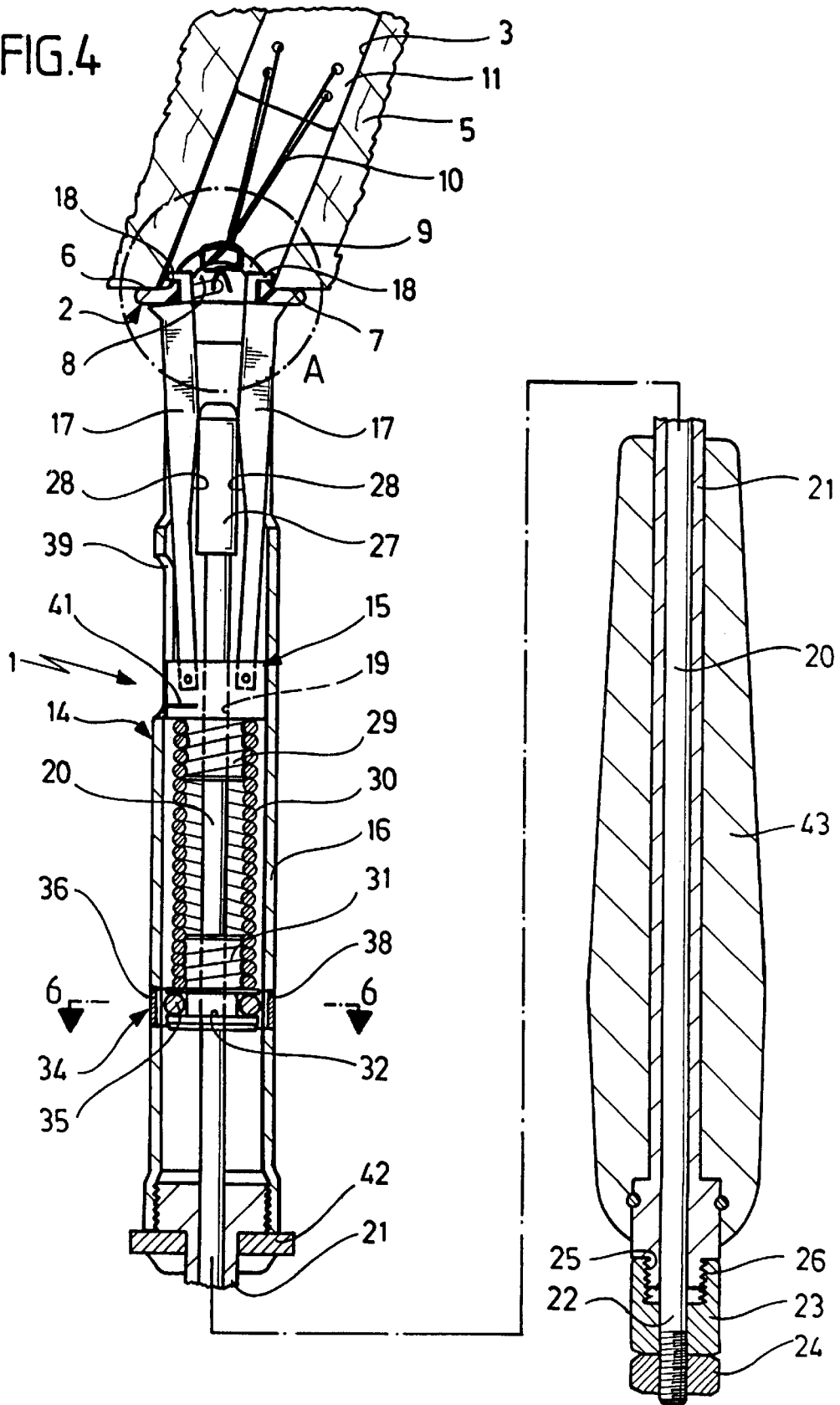

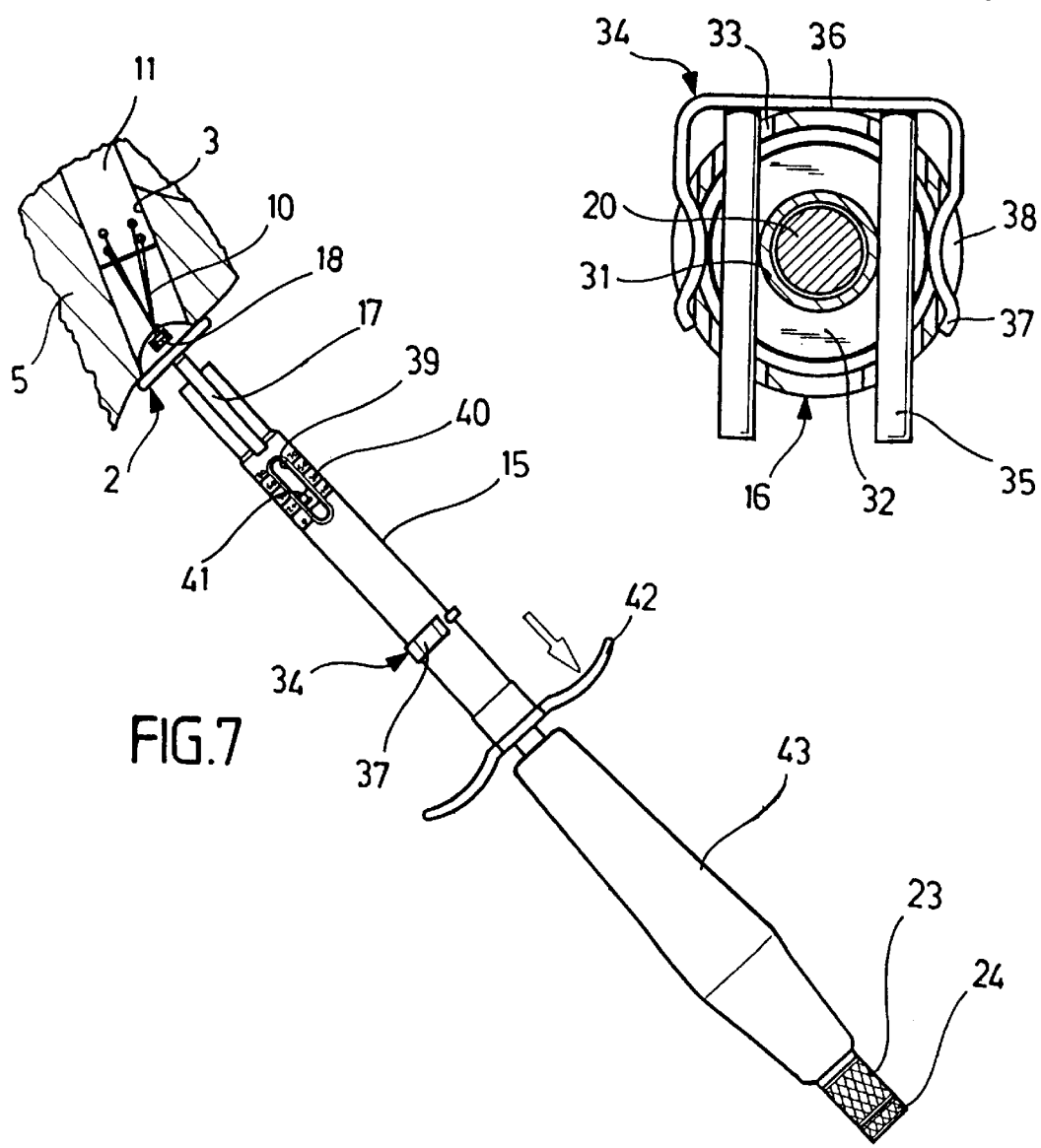

DEVICE AND METHOD FOR HANDLING AN IMPLANT COVERING A BONE TUNNEL

Figure 1:
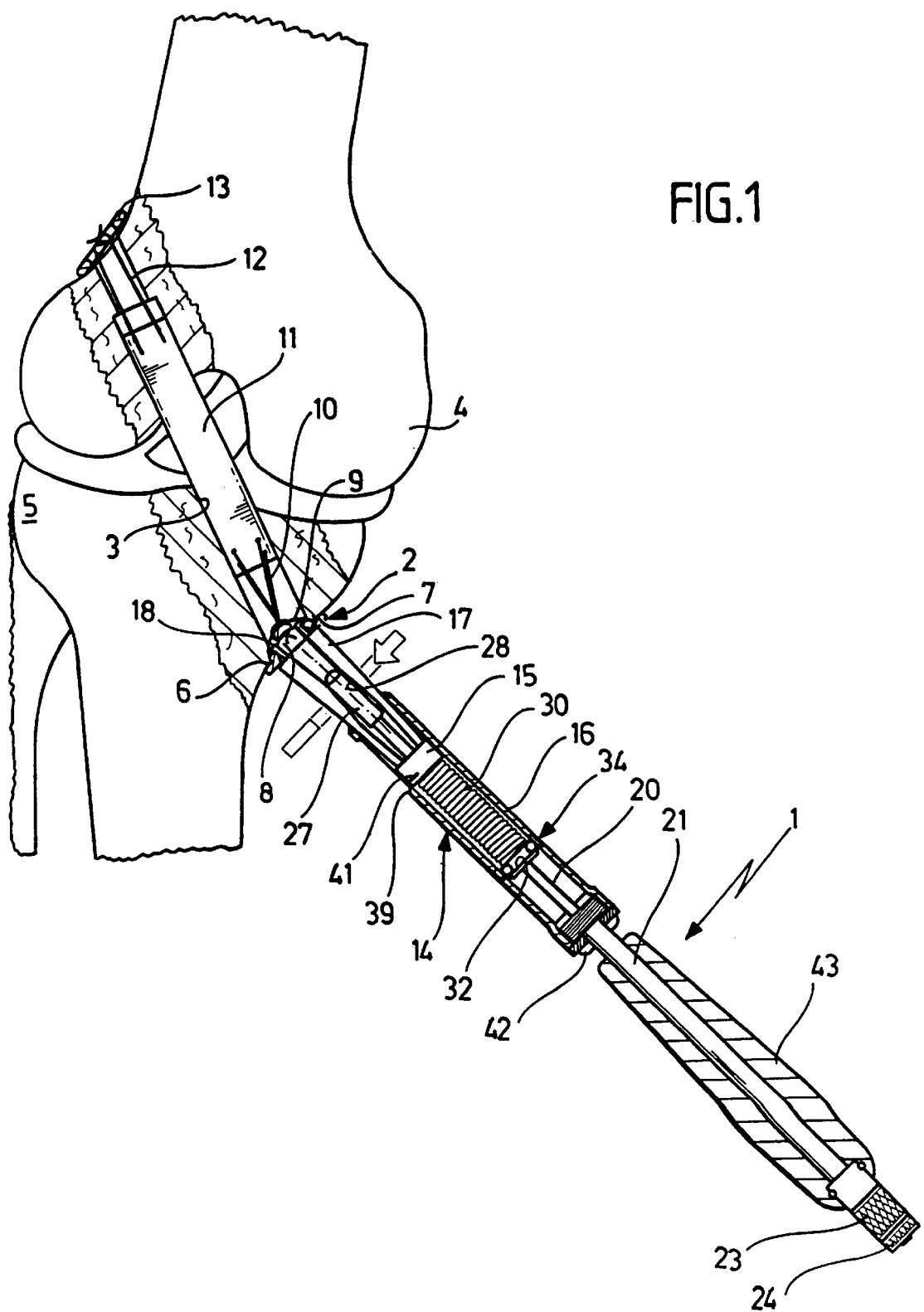

The present invention relates to the subject matter disclosed in German patent application 198 14 564.0 of Apr. 1, 1998, the entire specification of which is incorporated herein by reference.

The invention relates to a device for handling an implant which can be placed against a contact surface of a bone and thereby covers a tunnel in the bone and fixes in position at least one thread extending in the tunnel.

During the insertion of ligament replacement implants in the knee area, a ligament replacement implant is inserted in a tunnel passing through the head of the femur and the head of the tibia and is fixed on the bone via threads attached to it. For the purpose of fixing, disk-like or button-like implants are used which close the tunnel in the bone on the outside. The ligament replacement implant must be inserted into the tunnel in the bone with an exactly defined tension, and for this purpose it is known to vary the tension by turning the implants fixing the threads in position about the longitudinal axis of the bone tunnel. This turning leads to a twisting of the threads holding the ligament replacement implant and thus to an alteration in the tension.

The object of the invention is to propose a device for the handling of an implant of this type, with which the tension of the ligament replacement implant may be varied in the bone tunnel in a controlled manner.

This object is accomplished in accordance with the invention by a device of the type described at the outset which is characterized by releasable holding means on the device, with which the device can be connected to the implant in a locking position of the holding means in such a manner that as a result of rotation of the device the implant can be turned in relation to an axis defined by the tunnel and in addition lifted away from its contact surface in the direction of this axis.

Such a device can thus be temporarily connected to the implant such that any turning of the device leads to turning of the implant and therefore to a change in the twisting of the threads in the bone tunnel, i.e. to an alteration in the tension. Since the implant is pulled forcefully against the contact surface by the threads and since means for securing against rotation are customarily provided in the case of such implants in order to maintain tension once this has been reached, it is also possible with the new device to lift the implant slightly away from the contact surface for turning and thus make the turning possible. The implant is placed against the contact surface again only after the desired tension has been set; by releasing the holding means the connection between implant and device can be released again.

In a preferred embodiment it is provided for the holding means to comprise spreading elements which in their locking position engage the back of recesses on the implant.

The recesses can be formed, in particular, by the edges of openings in the implant. With such a solution, the spreading elements are guided through the openings of the implant and then spread apart so that, as a result, a form-locking connection results which enables the operator not only to lift the implant away from the contact surface of the bone but also to turn it in the desired manner as a result of movement of the device.

It is favorable when the spreading elements are spring arms which extend parallel to one another and may be moved away from one another at their free ends by means of a spreading member insertable between them.

The spreading member can, in particular, be displaceable on the device in longitudinal direction of the spring arms.

In a particularly preferred embodiment it is provided for the device to have an elongated, essentially cylindrical housing and for the spreading member to be connected to an actuating rod which is mounted in the housing for displacement in longitudinal direction and exits from the housing at its end remote from the spreading elements.

This actuating rod can have a grip at its free end.

It is particularly advantageous when it is provided in a preferred embodiment for the spreading elements to be connected via an elastic spring element to a pulling handle, with which a force lifting the implant away from the contact surface of the bone can be transferred to it. The lifting of the implant away from the contact surface thus takes place with a spring element as intermediate element.

This may be utilized, in particular, for the fact that a marking is provided for indicating the distance between the spreading elements and the pulling handle so that the operator can establish from this marking the force which is necessary to lift the implant away from the contact surface. This force is a measurement for the tension of the threads and the ligament replacement implant in the bone tunnel and thus gives the operator immediate information on whether the desired setting has been reached or not.

It may be provided, in particular, for the spreading elements to be mounted on a first housing portion of the device, for the pulling handle to be securely connected to a second housing portion of the device and for the two housing portions to be adapted to be pulled apart from one another contrary to the force of a spring connecting them.

In a preferred embodiment, the second housing portion can be designed in the shape of a sleeve and accommodate the first housing portion in it at least partially.

In this respect, it is advantageous when the spring is arranged in the interior of the second housing portion.

It is favorable when the spring is detachably connected to the second housing portion; the two housing portions can then be separated from one another simply by detaching the spring and so cleaning of all the parts of the device is possible without further ado.

A fixing element, in particular, in the shape of a U-shaped clip which can be inserted into the second housing portion through lateral openings therein can be provided for the detachable connection of the second housing portion and the spring.

It is, in addition, favorable when the spring is a helical spring, into which threaded connection pieces are screwed at its ends for the connection with the first and/or the second housing portion. These can also be screwed out of the spring so that a complete dismantling of the device for cleaning purposes can be achieved.

The application of the pulling force necessary for checking the tension of the ligament replacement is made easier when laterally projecting gripper bars are arranged on the second housing portion.

The marking can comprise, in particular, a window in the second housing portion and an indicator element on the first housing portion which is visible through the window.

The following description of preferred embodiments of the invention serves to explain the invention in greater detail in conjunction with the drawings. These show:

FIG. 1 a view of a knee joint with an inserted ligament replacement implant and a handling device applied to the fixation implant;

FIG. 2 a longitudinal sectional view through the handling device of FIG. 1 with the spreading elements in the release position;

FIG. 3 a view similar to FIG. 2 with a handling device turned through 90°;

FIG. 4 an enlarged longitudinal sectional view of the handling device with the spreading elements in locking position;

FIG. 5 a sectional view of an implant covering a tunnel in the bone with inserted spreading elements of the handling device;

FIG. 6 a sectional view along line 6—6 in FIG. 4 and

FIG. 7 a side view of the handling device connected to the implant during checking of the tension of the ligament replacement implant.

The instrument 1 shown in the drawings serves for the handling of a disk-like or button-like implant 2 which, in the illustrated embodiment, closes a tunnel 3 in the knee area, which penetrates the head 4 of the femur and the head 5 of the tibia, on one side at the end. The implant 2 thereby abuts with a flat edge 6 against the contact surface 7 of the bone surrounding the exit point of the tunnel 3 and is centered in the tunnel 3 by a central, inwardly curved bulge 8.

Two openings 9 are provided off-center in the implant 2 on opposite sides in the region of the bulge 8 and threads 10 are guided through them, these threads being connected, on the one hand, to a ligament replacement implant 11 in the interior of the tunnel 3 and, on the other hand, to the implant 2; a knot in the threads 10 may be accommodated in the sunken, central area of the implant 2.

The ligament implant 11 is likewise connected on the opposite side via threads 12 to a button-like or disk-like implant 13 which closes the tunnel 3 on the opposite side by abutting on the bone on the outside. In this way, the ligament replacement implant 11 is held in a tensioned manner by the threads 10 and 12 between the two implants 2 and 13 and extends over the greatest portion of the length of the tunnel 3 so that the ligament implant 11 can fuse permanently with the surrounding bone material over the course of time.

For the operation to succeed it is essential for the ligament replacement implant 11 to be tensioned in the tunnel 3 in exactly the desired manner, and in order to adjust this tension the instrument 1 illustrated in the drawings is used.

This instrument 1 has an elongated, cylindrical housing 14 with a cylindrical holder 15 and a sleeve 16 accommodating the holder 15 and open at the end.

The holder 15 supports two spring arms 17 which are arranged next to one another parallel to the longitudinal direction of the housing 14, protrude out of the open end of the sleeve 16 and bear at their free ends gripping elements 18 directed outwards in the shape of hooks.

A push rod 20 is mounted in a central longitudinal bore 19 of the holder 15 for longitudinal displacement and this penetrates the sleeve 16 and a guide tube 21 adjoining the sleeve completely. At its end 22 projecting out of the guide tube 21, a grip 23 milled on the outside is screwed onto the push rod 20 and secured by means of a counternut 24. The push rod 20 is mounted in the sleeve 16 for longitudinal displacement and can be displaced between a withdrawn position, in which the grip 23 is remote from the end of the guide tube 21, and an advanced position, in which the grip 23 abuts on the end of the guide tube 21. In this advanced position, the grip 23 can be secured on the guide tube 21 in that the grip 23 is screwed onto an external thread 26 of the guide tube 21 with an internal thread 25.

At the end located opposite the grip 23, the push rod 20 bears a spreading member 27 in the form of a cylinder member which can be inserted between the spring arms 17 as the push rod 20 is moved forwards and thereby abuts on guide surfaces 28 of the spring arms 17 which extend inwards at an angle so that the spring arms 17 are thereby spread radially outwards.

The holder 15 bears at its end remote from the spring arms 17 a bushing 29 with an external thread, onto which a helical spring 30 surrounding the push rod 20 in spaced relation thereto is screwed. A bushing 31 with an external thread is screwed into the opposite end of the helical spring 30 in a similar manner and has a circumferential annular groove 32 at its end remote from the helical spring 30. This bushing 31 with an external thread is secured on the sleeve 16 in axial direction in that a U-shaped bracket 34 with two parallel holding pins 35 and a crosspiece 36 connecting these holding pins 35 is inserted through off-center openings 33 in the sleeve 16 which are aligned with one another, wherein the holding pins 35 engage in the annular groove 32 of the bushing 31 with an external thread (FIG. 6). The bracket 34 is positioned in its position by resilient ends 37 of the crosspiece 36; the resilient ends 37 thereby engage in openings 38 in the sleeve 16 but they can be lifted flexibly out of these openings 38 with the use of a specific force so that the bracket 34 can then be drawn out of the openings 33 and releases the bushing 31 with an external thread.

An elongated window 39 is arranged laterally in the sleeve 16 and a measurement scale 40 is located next to it; a marking element 41, which is arranged on the bushing 29 with an external thread, is visible through this window 39, for example, a painted line.

At the end remote from the spring arms 17, the sleeve 16 has two radially projecting gripper bars 42 (FIG. 2); in addition, the guide tube 21 is surrounded by an elongated handle 43 which is held on the guide tube 21 so as to be axially non-displaceable.

As a result of this configuration, the housing 14 comprises two portions which are connected to one another by the helical spring 30 and can be displaced relative to one another in longitudinal direction, namely a first housing portion formed by the holder 15 and the spring arms 17 held thereon as well as the bushing 29 with an external thread and a second housing portion formed by the sleeve 16, the guide tube 21, the handle 43 and the bushing 31 with an external thread. These two housing portions can be pulled apart from one another contrary to the force of the helical spring 30 so that the spring arms 17 project further out of the sleeve 16; the extent of the extension of the entire housing 14 as a result of this pulling apart of the housing portions may be read from the displacement of the marking element 41 in the window 39.

The instrument described is used to adjust the tension of the ligament replacement implant 11 in a controlled manner.

For this purpose, the gripping elements 18 of the instrument 1 are inserted through the openings 9 of the implant 2 after insertion of the ligament replacement implant 11 and the implants 2 and 13 and the insertion of the threads 10 and 12. This takes place with a retracted push rod 20, i.e. with the spring arms 17 in the non-spread release position.

As soon as the gripping elements 18 are inserted through the opening 9, the push rod 20 is pushed forwards so that the spreading member 27 spreads the spring arms 17 outwards as a result of abutment on the guide surfaces 28 thereof and presses the gripping elements 18 engaging laterally behind the openings 9 against the edge of the openings 9 (FIG. 5). As a result, a secure connection is provided between the gripping elements 18 and the implant 2.

In order to increase the tension of the ligament implant 11, the implant 2 is turned about the longitudinal axis of the tunnel 3 by means of the instrument 1 applied in this way so that the threads 10, 12 are twisted. For this purpose, the implant 2 may be lifted slightly away from the contact surface 7 in order to, where applicable, make means for securing against rotation effective at this point ineffective for the turning.

During this twisting procedure the surgeon can ascertain at any moment how great the tension of the ligament replacement implant 11 is. For this purpose it is sufficient to displace the instrument 1 in the direction of the tunnel 3 at the handle 43 and, where applicable, at the gripping bars 42. As a result, a force lifting the implant 2 away from the contact surface 7 is exerted on it and this counteracts the tension of the ligament replacement implant 11. The surgeon increases this force for such a time until the implant 2 is lifted slightly away from the contact surface 7, and in this position he can observe the displacement of the marking element 41 in relation to the measurement scale 40 next to the window 39. This displacement is a measurement for the extension of the helical spring 30 and thus a measurement for the force, with which the ligament replacement implant 11 draws the implant 2 against the contact surface 7, i.e. for the tension of the ligament replacement implant 11.

By turning the implant 2 in the manner described, this tension may be altered, and the surgeon may observe this alteration in the tension immediately from the displacement of the marking element 41 in the window 39. As soon as the correct tension is reached, the implant 2 is placed on the contact surface 7 again, and the instrument 1 may be withdrawn simply by retracting the push rod 20. As a result, the spreading member 27 between the spring arms 17 is drawn back and enables the spring arms 17 to move radially inwards. The instrument can be removed in this position; the gripping elements 18 may easily be guided through the openings 9 in this released position of the spring arms 17.

An essential advantage of the construction of the instrument 1 as described is also to be seen in the fact that this may easily be dismantled into its individual parts. For this purpose, it is sufficient to pull the bracket 34 out of the openings 33; the two housing portions can then be separated from one another. In addition, it is possible to remove the helical spring 30 quite easily since this is only screwed onto the bushings 29 and 31 with external threads. In this way, the spring may, for example, be exchanged when other spring characteristics are desired.

By unscrewing the counternut 24 and the grip 23, the push rod 20 can then be pulled completely out of the guide tube 21 so that the individual parts of this instrument can be cleaned in an effective manner.

In this respect, it is helpful when the guide tube 21 and the sleeve 16 are separate parts which, as realized in the illustrated embodiment, are screwed to one another.

What is claimed is:

1. A device for handling an implant adapted to be placed against a contact surface of a bone to cover a tunnel in the bone and fix in position at least one thread extending in the tunnel, comprising:
   a handle;
   releasable holding means operatively associated with said handle for connecting said device to the implant in a locking position, such that by rotating the device the implant can be turned in relation to an axis defined by said tunnel and can also be lifted away from the contact surface in the direction of said axis.

2. A device as defined in claim 1, wherein the holding means comprise spreading elements adapted to engage the back of recesses on the implant in the locking position.

3. A device as defined in claim 2, wherein the recesses are formed by the edges of openings in the implant.

4. A device as defined in claim 2, wherein the spreading elements comprise spring arms extending parallel to one another, said arms being movable away from one another at their free ends by means of a spreading member insertable between them.

5. A device as defined in claim 4, wherein the spreading member is displaceable on the device in a longitudinal direction of the spring arms.

6. A device as defined in claim 5 further comprising an elongated, essentially cylindrical housing;
   wherein the spreading member is connected to an actuating rod mounted in the housing for displacement in said longitudinal direction,
   said actuating rod exiting from the housing at an end remote from the spreading elements.

7. A device as defined in claim 6, wherein said actuating rod has a grip at a free end thereof.

8. A device as defined in claim 1, wherein the holding means are connected to a pulling handle via an elastic spring element, wherein a force for lifting the implant away from the contact surface of the bone is transferable by said pulling handle.

9. A device as defined in claim 8, wherein a marking is provided to indicate the distance between the holding means and the pulling handle.

10. A device as defined in claim 8, wherein:
    the holding means are mounted on a first housing portion of the device;
    the pulling handle is securely connected to a second housing portion of the device; and
    the two housing portions are adapted to be pulled apart from one another contrary to the force of a spring connecting them.

11. A device as defined in claim 10, wherein the second housing portion is designed in the shape of a sleeve that at least partially accommodates the first housing portion.

12. A device as defined in claim 11 wherein the spring is arranged in an interior of the second housing portion.

13. A device as defined in claim 12, wherein the spring is detachably connected to the second housing portion.

14. A device as defined in claim 13, wherein a fixing element insertable into the second housing portion through lateral openings therein is provided for the detachable connection of the second housing portion and the spring.

15. A device as defined in claim 14, wherein the fixing element is a U-shaped clip.

16. A device as defined in claim 10, wherein:
    said spring is a helical spring; and
    threaded connection pieces are screwed into said spring at its ends for connection to at least one of the first and second housing portions.

17. A device as defined in claim 10, further comprising laterally projecting gripper bars arranged on the second housing portion.

18. A device as defined in claim 10, wherein a marking is provided to indicate the distance between the holding means and the pulling handle, said marking comprising a window in the second housing and an indicator element visible through the window on the first housing portion.

19. A method for handling an implant adapted to be placed against a contact surface of a bone to cover a tunnel in the bone and fix in position at least one thread extending in the tunnel, comprising the steps of:
    releasably connecting the implant to a handling device,
    using the handling device to turn the implant about a longitudinal axis of the tunnel to alter the tension of the at least one thread extending in the tunnel, wherein the implant is turned until a desired tension of the at least one thread is reached.

20. A method as defined in claim 19, wherein the implant is slightly lifted away from the contact surface prior to the turning with the handling device, in order to render means for securing the implant against rotation ineffective during the turning of the implant.

21. A method as defined in claim 20, comprising the further step of slightly lifting the implant away from the contact surface using the handling device to check the tension of the at least one thread.

22. A method as defined in claim 21, wherein the tension of the at least one thread is checked by:
   pulling apart two parts of the handling device contrary to the force of a spring drawing the parts together, and
   observing the distance between the parts as a function of said tension.

23. A method as defined in claim 22, wherein when the desired tension is reached, the implant is placed on the contact surface using the handling device.

24. A method as defined in claim 19, comprising the further step of slightly lifting the implant away from the contact surface using the handling device to check the tension of the at least one thread.

25. A method as defined in claim 24, wherein the tension of the at least one thread is checked by:
   pulling apart two parts of the handling device contrary to the force of a spring drawing the parts together, and
   observing the distance between the parts as a function of said tension.

26. A method as defined in claim 25, wherein when the desired tension is reached, the implant is placed on the contact surface using the handling device.

* * * * *